United States Patent
Zentz et al.

(10) Patent No.: US 8,524,878 B1
(45) Date of Patent: Sep. 3, 2013

(54) METHODS OF IDENTIFYING AN ORGANISM

(75) Inventors: Emily B. Zentz, Germantown, MD (US); Colin William Dykes, Albuquerque, NM (US); Adam Michael Briska, Madison, WI (US)

(73) Assignee: OpGen, Inc., Gaithersburg, MD (US)

( * ) Notice: Subject to any disclaimer, the term of this patent is extended or adjusted under 35 U.S.C. 154(b) by 0 days.

(21) Appl. No.: 13/190,955

(22) Filed: Jul. 26, 2011

Related U.S. Application Data

(63) Continuation-in-part of application No. 12/120,586, filed on May 14, 2008.

(60) Provisional application No. 61/029,816, filed on Feb. 19, 2008.

(51) Int. Cl.
*C07H 21/04* (2006.01)
*C12Q 1/00* (2006.01)
*C12Q 1/68* (2006.01)

(52) U.S. Cl.
USPC .......... 536/24.32; 536/23.1; 536/23.7; 435/4; 435/6

(58) Field of Classification Search
USPC .............. 435/4, 6; 536/23.1, 23.7, 24.32
See application file for complete search history.

(56) References Cited

U.S. PATENT DOCUMENTS

2005/0272106 A1 12/2005 Moore et al.

OTHER PUBLICATIONS

International Search Report and Written Opinion for PCT/US12/48137, mailed Oct. 6. 2012
Zhang et al., Appl Environ Microbiol, 70(2):913-920, 2004.
Bruce et al., Proc, Nati, Acad. Sci., 92:5229-5233, 1995.
Gaillot et al., Molecular Microbiology, 35(6):1286-1294, 2000.
Roche et al., Infection and Immunity, 71(6):3429-3436, 2003.

*Primary Examiner* — Rodney P. Swartz
(74) *Attorney, Agent, or Firm* — Thomas C. Meyers; Brown Rudnick LLP

(57) ABSTRACT

This disclosure features methods of identifying an organism. In certain embodiments, the invention provides methods of distinguishing virulent and non-virulent strains of *Listeria monocytogenes*.

8 Claims, 11 Drawing Sheets

METHODS OF IDENTIFYING AN ORGANISM

RELATED APPLICATION

This application is a continuation-in-part of U.S. nonprovisional patent application Ser. No. 12/120,586 filed May 14, 2008, which claims priority to and the benefit of U.S. provisional application Ser. No. 61/029,816 filed Feb. 19, 2008, the content of each of which is incorporated by reference herein in its entirety.

TECHNICAL FIELD

This disclosure relates to methods of identifying an organism, e.g., a microorganism. The methods can include imaging nucleic acid of the organism.

BACKGROUND

Physical mapping of genomes, e.g., using restriction endonucleases to develop restriction maps, can provide accurate information about the nucleic acid sequences of various organisms. Restriction maps of, e.g., deoxyribonucleic acid (DNA), can be generated by optical mapping. Optical mapping can produce ordered restriction maps by using fluorescence microscopy to visualize restriction endonuclease cutting events on individual labeled DNA molecules.

SUMMARY

The present invention provides methods of identifying an organism, e.g., a microorganism. The methods include obtaining a restriction map of a nucleic acid from an organism and correlating the restriction map of the nucleic acid with a restriction map database, thereby identifying the organism. With use of a detailed restriction map database, the organism can be identified and classified not just at a genus and species level, but also at a sub-species (strain), a sub-strain, and/or an isolate level. The featured methods offer fast, accurate, and detailed information for identifying organisms. The methods can be used in a clinical setting, e.g., a human or veterinary setting; or in an environmental or industrial setting (e.g., clinical or industrial microbiology, food safety testing, ground water testing, air testing, contamination testing, and the like). In essence, the invention is useful in any setting in which the detection and/or identification of a microorganism is necessary or desirable.

This invention also features methods of diagnosing a disease or disorder in a subject by, inter alia, identifying an organism by correlating the restriction map of a nucleic acid from the organism with a restriction map database and correlating the identity of the organism with the disease or disorder.

In one aspect, the invention provides a method of identifying an organism. The method includes obtaining a restriction digest of a nucleic acid sample, imaging the restriction fragments, and comparing the imaged data to a database. Restriction maps of the invention can be ordered by, for example, attaching nucleic acids to a surface, elongating them on the surface and exposing to one or more restriction endonucleases. Generally, preferred methods of the invention comprise obtaining a nucleic acid sample from an organism; imaging the nucleic acid; obtaining a restriction map of the nucleic acid; and correlating the restriction map of the nucleic acid with a restriction map database, thereby identifying the organism.

The detected organism can be a microorganism, a bacterium, a protist, a virus, a fungus, or disease-causing organisms including microorganisms such as protozoa and multicellular parasites. The nucleic acid can be deoxyribonucleic acid (DNA), a ribonucleic acid (RNA) or can be a cDNA copy of an RNA obtained from a sample. The nucleic acid sample includes any tissue or body fluid sample, environmental sample (e.g., water, air, dirt, rock, etc.), and all samples prepared therefrom.

Methods of the invention can further include digesting nucleic acid with one or more enzymes, e.g., restriction endonucleases, e.g., BglII, NcoI, XbaI, and BamHI, prior to imaging. Preferred restriction enzymes include, but are not limited to:

| | | |
|---|---|---|
| AflII | ApaLI | BglII |
| AflII | BglII | NcoI |
| ApaLI | BglII | NdeI |
| AflII | BglII | MluI |
| AflII | BglII | PacI |
| AflII | MluI | NdeI |
| BglII | NcoI | NdeI |
| AflII | ApaLI | MluI |
| ApaLI | BglII | NcoI |
| AflII | ApaLI | BamHI |
| BglII | EcoRI | NcoI |
| BglII | NdeI | PacI |
| BglII | Bsu36I | NcoI |
| ApaLI | BglII | XbaI |
| ApaLI | MluI | NdeI |
| ApaLI | BamHI | NdeI |
| BglII | NcoI | XbaI |
| BglII | MluI | NcoI |
| BglII | NcoI | PacI |
| MluI | NcoI | NdeI |
| BamHI | NcoI | NdeI |
| BglII | PacI | XbaI |
| MluI | NdeI | PacI |
| Bsu36I | MluI | NcoI |
| ApaLI | BglII | NheI |
| BamHI | NdeI | PacI |
| BamHI | Bsu36I | NcoI |
| BglII | NcoI | PvuII |
| BglII | NcoI | NheI |
| BglII | NheI | PacI |

Imaging ideally includes labeling the nucleic acid. Labeling methods are known in the art and can include any known label. However, preferred labels are optically-detectable labels, such as 4-acetamido-4'-isothiocyanatostilbene-2, 2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron® Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; naphthalo cyanine, BOBO, POPO, YOYO, TOTO and JOJO.

A database for use in the invention can include a restriction map similarity cluster. The database can include a restriction map from at least one member of the clade of the organism. The database can include a restriction map from at least one subspecies of the organism. The database can include a restriction map from a genus, a species, a strain, a sub-strain, or an isolate of the organism. The database can include a restriction map with motifs common to a genus, a species, a strain, a sub-strain, or an isolate of the organism.

In another aspect, the invention features a method of diagnosing a disease or disorder in a subject, including obtaining a sample suspected to contain an organism to be detected; (b) imaging a nucleic acid from the organism; (c) obtaining a restriction map of the nucleic acid; (d) identifying the organism by correlating the restriction map of the nucleic acid with a restriction map database; and (e) correlating the identity of the organism with the disease or disorder.

Methods can further include treating a disease or disorder in a subject, including diagnosing a disease or disorder in the subject as described above and providing treatment to the subject to ameliorate the disease or disorder. Treatment can include administering a drug to the subject.

In one embodiment, a restriction map obtained from a single DNA molecule is compared against a database of restriction maps from known organisms in order to identify the closest match to a restriction fragment pattern occurring in the database. This process can be repeated iteratively until sufficient matches are obtained to identify an organism at a predetermined confidence level. According to methods of the invention, nucleic acid from a sample are prepared and imaged as described herein. A restriction map is prepared and the restriction pattern is correlated with a database of restriction patterns for known organisms. In a preferred embodiment, organisms are identified from a sample containing a mixture of organisms. In a highly-preferred embodiment, methods of the invention are used to determine a ratio of various organisms present in a sample suspected to contain more than one organism. Moreover, use of methods of the invention allows the detection of multiple microorganisms from the same sample, either serially or simultaneously.

In use, the invention can be applied to identify a microorganism making up a contaminant in an environmental sample. For example, methods of the invention are useful to identify a potential biological hazard in a sample of air, water, soil, clothing, luggage, saliva, urine, blood, sputum, food, drink, and others. In a preferred embodiment, methods of the invention are used to detect and identify an organism in a sample obtained from an unknown source. In essence, methods of the invention can be used to detect biohazards in any environmental or industrial setting.

Further aspects and features of the invention will be apparent upon inspection of the following detailed description thereof.

All patents, patent applications, and references cited herein are incorporated in their entireties by reference.

DETAILED DESCRIPTION

Figure 1:
FIG. 1 is a diagram showing restriction maps of six isolates of *E. coli*.

The present disclosure features methods of identifying an organism, e.g., a microorganism. The methods include obtaining a restriction map of a nucleic acid, e.g., DNA, from an organism and correlating the restriction map of the nucleic acid with a restriction map database, thereby identifying the organism. With use of a detailed restriction map database that contains motifs common to various groups and sub-groups, the organism can be identified and classified not just at a genus and species level, but also at a sub-species (strain), a sub-strain, and/or an isolate level. For example, bacteria can be identified and classified at a genus level, e.g., *Escherichia* genus, species level, e.g., *E. coli* species, a strain level, e.g., O157, CFT, and K12 strains of *E. coli*, and isolates, e.g., O157:H7 isolate of *E. coli* (as described in Experiment 3B below). The featured methods offer a fast, accurate, and detailed information for identifying organisms. These methods can be used in a variety of clinical settings, e.g., for identification of an organism in a subject, e.g., a human or an animal subject.

This disclosure also features methods of diagnosing a disease or disorder in a subject by, inter alia, identifying an organism via correlating the restriction map of a nucleic acid from the organism with a restriction map database, and correlating the identity of the organism with the disease or disorder. These methods can be used in a clinical setting, e.g., human or veterinary setting.

Methods of the invention are also useful for identifying and/or detecting an organism in food or in an environmental setting. For example, methods of the invention can be used to assess an environmental threat in drinking water, air, soil, and other environmental sources. Methods of the invention are also useful to identify organisms in food and to determine a common source of food poisoning in multiple samples that are separated in time or geographically, as well as samples that are from the same or similar batches.

Restriction Mapping

The methods featured herein utilize restriction mapping during both generation of the database and processing of an organism to be identified. One type of restriction mapping that can be used is optical mapping. Optical mapping is a single-molecule technique for production of ordered restriction maps from a single DNA molecule (Samad et al., *Genome Res.* 5:1-4, 1995). During this method, individual fluorescently labeled DNA molecules are elongated in a flow of agarose between a coverslip and a microscope slide (in the first-generation method) or fixed onto polylysine-treated glass surfaces (in a second-generation method). Id. The added endonuclease cuts the DNA at specific points, and the fragments are imaged. Id. Restriction maps can be constructed based on the number of fragments resulting from the digest. Id. Generally, the final map is an average of fragment sizes derived from similar molecules. Id. Thus, in one embodiment of the present methods, the restriction map of an organism to be identified is an average of a number of maps generated from the sample containing the organism.

Optical mapping and related methods are described in U.S. Pat. No. 5,405,519, U.S. Pat. No. 5,599,664, U.S. Pat. No. 6,150,089, U.S. Pat. No. 6,147,198, U.S. Pat. No. 5,720,928, U.S. Pat. No. 6,174,671, U.S. Pat. No. 6,294,136, U.S. Pat. No. 6,340,567, U.S. Pat. No. 6,448,012, U.S. Pat. No. 6,509,158, U.S. Pat. No. 6,610,256, and U.S. Pat. No. 6,713,263, each of which is incorporated by reference herein. Optical Maps are constructed as described in Reslewic et al., Appl Environ Microbiol. 2005 September; 71 (9):5511-22, incorporated by reference herein. Briefly, individual chromosomal fragments from test organisms are immobilized on derivatized glass by virtue of electrostatic interactions between the negatively-charged DNA and the positively-charged surface, digested with one or more restriction endonuclease, stained with an intercalating dye such as YOYO-1 (Invitrogen) and positioned onto an automated fluorescent microscope for image analysis. Since the chromosomal fragments are immobilized, the restriction fragments produced by digestion with the restriction endonuclease remain attached to the glass and can be visualized by fluorescence microscopy, after staining with the intercalating dye. The size of each restriction fragment in a chromosomal DNA molecule is measured using image analysis software and identical restriction fragment patterns in different molecules are used to assemble ordered restriction maps covering the entire chromosome.

Restriction Map Database

The database(s) used with the methods described herein can be generated by optical mapping techniques discussed supra. The database(s) can contain information for a large number of isolates, e.g., about 200, about 300, about 400, about 500, about 600, about 700, about 800, about 900, about 1,000, about 1,500, about 2,000, about 3,000, about 5,000, about 10,000 or more isolates. In addition, the restriction maps of the database contain annotated information (a similarity cluster) regarding motifs common to genus, species, sub-species (strain), sub-strain, and/or isolates for various organisms. The large number of the isolates and the information regarding specific motifs allows for accurate and rapid identification of an organism.

The restriction maps of the database(s) can be generated by digesting (cutting) nucleic acids from various isolates with specific restriction endonuclease enzymes. Some maps can be a result of digestion with one endonuclease. Some maps can be a result of a digest with a combination of endonucleases, e.g., two, three, four, five, six, seven, eight, nine, ten or more endonucleases. The exemplary endonucleases that can be used to generate restriction maps for the database(s) and/or the organism to be identified include: BglII, NcoI, XbaI, and BamHI. Non-exhaustive examples of other endonucleases that can be used include: AluI, ClaI, DpnI, EcoRI, HindIII, KpnI, PstI, SacI, and SmaI. Yet other restriction endonucleases are known in the art.

Map alignments between different strains are generated with a dynamic programming algorithm which finds the optimal alignment of two restriction maps according to a scoring model that incorporates fragment sizing errors, false and missing cuts, and missing small fragments (See Myers et al., Bull Math Biol 54:599-618 (1992); Tang et al., J Appl Probab 38:335-356 (2001); and Waterman et al., Nucleic Acids Res 12:237-242). For a given alignment, the score is proportional to the log of the length of the alignment, penalized by the differences between the two maps, such that longer, better-matching alignments will have higher scores.

To generate similarity clusters, each map is aligned against every other map. From these alignments, a pair-wise alignment analysis is performed to determine "percent dissimilarity" between the members of the pair by taking the total length of the unmatched regions in both genomes divided by the total size of both genomes. These dissimilarity measurements are used as inputs into the agglomerative clustering method "Agnes" as implemented in the statistical package "R". Briefly, this clustering method works by initially placing each entry in its own cluster, then iteratively joining the two nearest clusters, where the distance between two clusters is the smallest dissimilarity between a point in one cluster and a point in the other cluster.

Organisms to be Identified

Various organisms, e.g., viruses, and various microorganisms, e.g., bacteria, protists, and fungi, can be identified with the methods featured herein. In one embodiment, the organism's genetic information is stored in the form of DNA. The genetic information can also be stored as RNA.

The sample containing the organism to be identified can be a human sample, e.g., a tissue sample, e.g., epithelial (e.g., skin), connective (e.g., blood and bone), muscle, and nervous tissue, or a secretion sample, e.g., saliva, urine, tears, and feces sample. The sample can also be a non-human sample, e.g., a horse, camel, llama, cow, sheep, goat, pig, dog, cat, weasel, rodent, bird, reptile, and insect sample. The sample can also be from a plant, water source, food, air, soil, plants, or other environmental or industrial sources.

Identifying an Organism

The methods described herein, i.e., methods of identifying an organism, diagnosing a disease or disorder in a subject, determining antibiotic resistance of an organism, determining an antibiotic resistance profile of a bacterium, and determining a therapeutically effective antibiotic to administer to a subject, and treating a subject, include correlating the restriction map of a nucleic acid of an organism with a restriction map database. The methods involve comparing each of the raw single molecule maps from the unknown sample (or an average restriction map of the sample) against each of the entries in the database, and then combining match probabilities across different molecules to create an overall match probability.

In one embodiment of the methods, entire genome of the organism to be identified can be compared to the database. In another embodiment, several methods of extracting shared elements from the genome can be created to generate a reduced set of regions of the organism's genome that can still serve as a reference point for the matching algorithms.

As discussed above and in the Examples below, the restriction maps of the database can contain annotated information (a similarity cluster) regarding motifs common to genus, species, sub-species (strain), sub-strain, and/or isolates for various organisms. Such detailed information would allow identification of an organism at a sub-species level, which, in turn, would allow for a more accurate diagnosis and/or treatment of a subject carrying the organism.

In another embodiment, methods of the invention are used to identify genetic motifs that are indicative of an organism, strain, or condition. For example, methods of the invention are used to identify in an isolate at least one motif that confers antibiotic resistance. This allows appropriate choice of treatment without further cluster analysis.

Applications

The methods described herein can be used in a variety of settings, e.g., to identify an organism in a human or a non-human subject, in food, in environmental sources (e.g., food, water, air), and in industrial settings. The featured methods also include methods of diagnosing a disease or disorder in a subject, e.g., a human or a non-human subject, and treating the subject based on the diagnosis. The method includes: obtaining a sample comprising an organism from the subject; imaging a nucleic acid from the organism; obtaining a restriction map of said nucleic acid; identifying the organism by correlating the restriction map of said nucleic acid with a restriction map database; and correlating the identity of the organism with the disease or disorder.

As discussed above, various organisms can be identified by the methods discussed herein and therefore various diseases and disorders can be diagnosed by the present methods. The organism can be, e.g., a cause, a contributor, and/or a symptom of the disease or disorder. In one embodiment, more than one organism can be identified by the methods described herein, and a combination of the organisms present can lead to diagnosis. Skilled practitioners would be able to correlate the identity of an organism with a disease or disorder. For example, the following is a non-exhaustive list of some diseases and bacteria known to cause them: tetanus—*Clostridium tetani*; tuberculosis—*Mycobacterium tuberculosis*; meningitis—*Neisseria meningitidis*; botulism—*Clostridium botulinum*; bacterial dysentry—*Shigella dysenteriae*; lyme disease—*Borrelia burgdorferi*; gasteroenteritis—*E. coli* and/or *Campylobacter* spp.; food poisoning—*Clostridium perfringens, Bacillus cereus, Salmonella enteriditis*, and/or *Staphylococcus aureus*. These and other diseases and disorders can be diagnosed by the methods described herein.

Once a disease or disorder is diagnosed, a decision about treating the subject can be made, e.g., by a medical provider or a veterinarian. Treating the subject can involve administering a drug or a combination of drugs to ameliorate the disease or disorder to which the identified organism is contributing or of which the identified organism is a cause. Amelioration of the disease or disorder can include reduction in the symptoms of the disease or disorder. The drug administered to the subject can include any chemical substance that affects the processes of the mind or body, e.g., an antibody and/or a small molecule, The drug can be administered in the form of a composition, e.g., a composition comprising the drug and a pharmaceutically acceptable carrier. The composition can be in a form suitable for, e.g., intravenous, oral, topical, intramuscular, intradermal, subcutaneous, and anal administration. Suitable pharmaceutical carriers include, e.g., sterile saline, physiological buffer solutions and the like. The pharmaceutical compositions may be additionally formulated to control the release of the active ingredients or prolong their presence in the patient's system. Numerous suitable drug delivery systems are known for this purpose and include, e.g., hydrogels, hydroxmethylcellulose, microcapsules, liposomes, microemulsions, microspheres, and the like. Treating the subject can also include chemotherapy and radiation therapy.

Identifying Virulent and Low- or Non-Virulent Stains of *Listeria monocytogenes*

*Listeria monocytogenes* is an organism that causes a Listeriosis infection, which is one of the leading causes of death from food-borne pathogens, especially in pregnant women, newborns, elderly, and immuno-compromised individuals. It is found in environments such as decaying vegetable matter, sewage, water, and soil, and it can survive extremes of both temperatures (from about 1° C. to about 45° C.) and salt concentration. Due to these characteristics, *L. monocytogenes* is an extremely dangerous food-born pathogen, especially in food that is not reheated. The bacterium can spread from an infection site in the intestines to the central nervous system and, in the case of a pregnant woman, to the fetal-placental unit.

Meningitis (inflammation of the membrane surrounding spinal cord and brain), gastroenteritis (inflammation of mucous membranes of stomach and intestine), and septicemia (systemic spread of bacteria and toxins in the blood) can result from infection. This organism is enteroinvasive, and utilizes an actin-based motility system by using a surface protein, ActA, that promotes actin polymerization, to spread intercellularly using the polymerized cytoskeletal protein as a motor. There are 13 serovars associated with *L. monocytogenes*, and the serovar 4b strains are more commonly associated with invasive disease.

Methods of the invention were used to obtain optical maps of strains of *L. monocytogenes* that are known to be virulent or low- or non-virulent. Optical maps were obtained for the following strains: *L. monocytogenes* BO43; *L. monocytogenes* 416; *L. monocytogenes* strain 4b F2365; *L. monocytogenes* strain EGD-e; *L. monocytogenes* strain A23; *L. monocytogenes* Clip81459 '4b CLIP80459'. *L. monocytogenes* strain 4b F2365 is a highly virulent strain of *L. monocytogenes* that is of serotype 4b. This strain was isolated in 1985 in California, USA, during an outbreak of listeriosis among patients with AIDS. The strain is of serotype 4b and was isolated from a cheese product that caused the outbreak. *L. monocytogenes* Clip81459 '4b CLIP80459' and *L. monocytogenes* (A23) are also highly virulent strains of *L. monocytogenes* of serotype 4b. *L. monocytogenes* strain EGD-e is a highly virulent strain of *L. monocytogenes*. This strain has numerous pathogenicity islands and genes, and is serovar 1/2a. This strain is derived from the strain EGD that was used in studies of cell-mediated immunity. *L. monocytogenes* BO43; *L. monocytogenes* 416 are low- and/or non-virulent strains of *L. monocytogenes*.

Figure 9A:
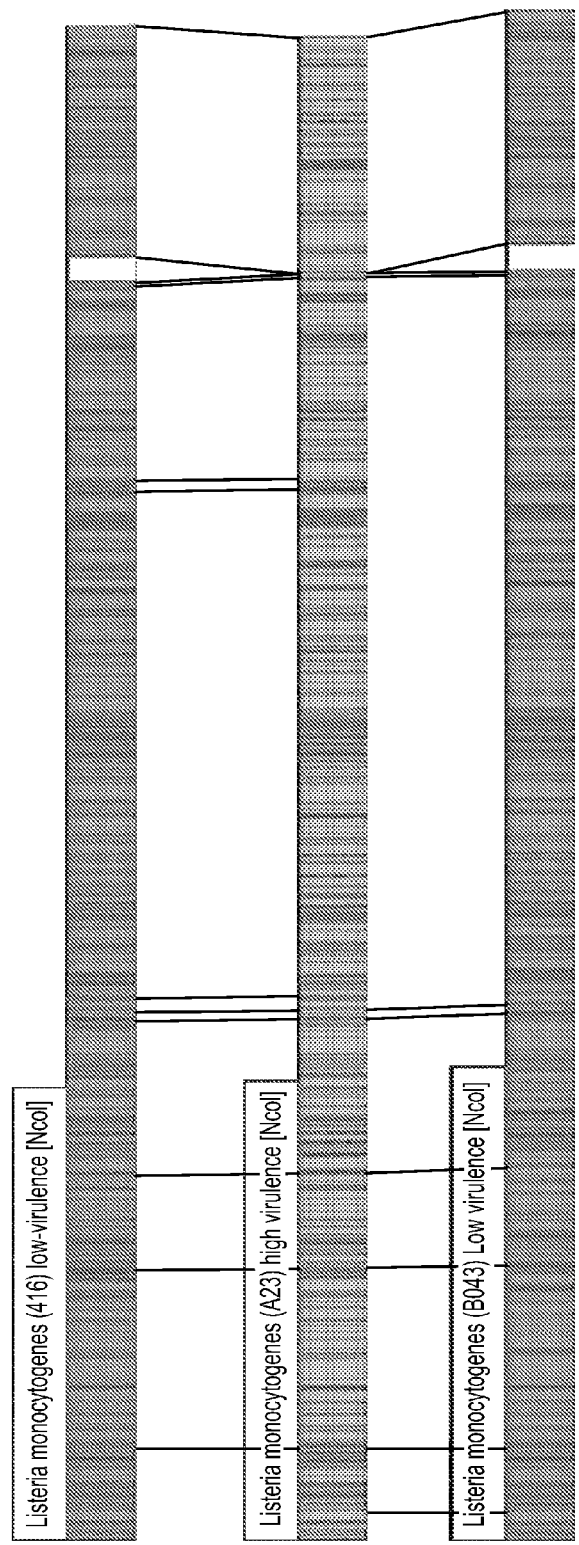
FIG. 9 panel A is a set of three optical maps showing a whole genome comparison between three Group III strains of *L. monocytogenes*. The A23 strain is highly virulent while the BO43 and the 416 strains are of low- or non-virulence. The maps show that the only difference discovered is a 48.3 kb region. Panel B is a set of three optical maps showing strains BO43 and 416 compared to a strain of EGD-e. Similar to the comparison in panel A, the only difference between the EDG-e strain and the BO43 and the 416 strains is the 48.3 kb insertion in the BO43 and the 416 strains. Panel C shows an optical map of the 48.3 kb region.
Figure 9B:
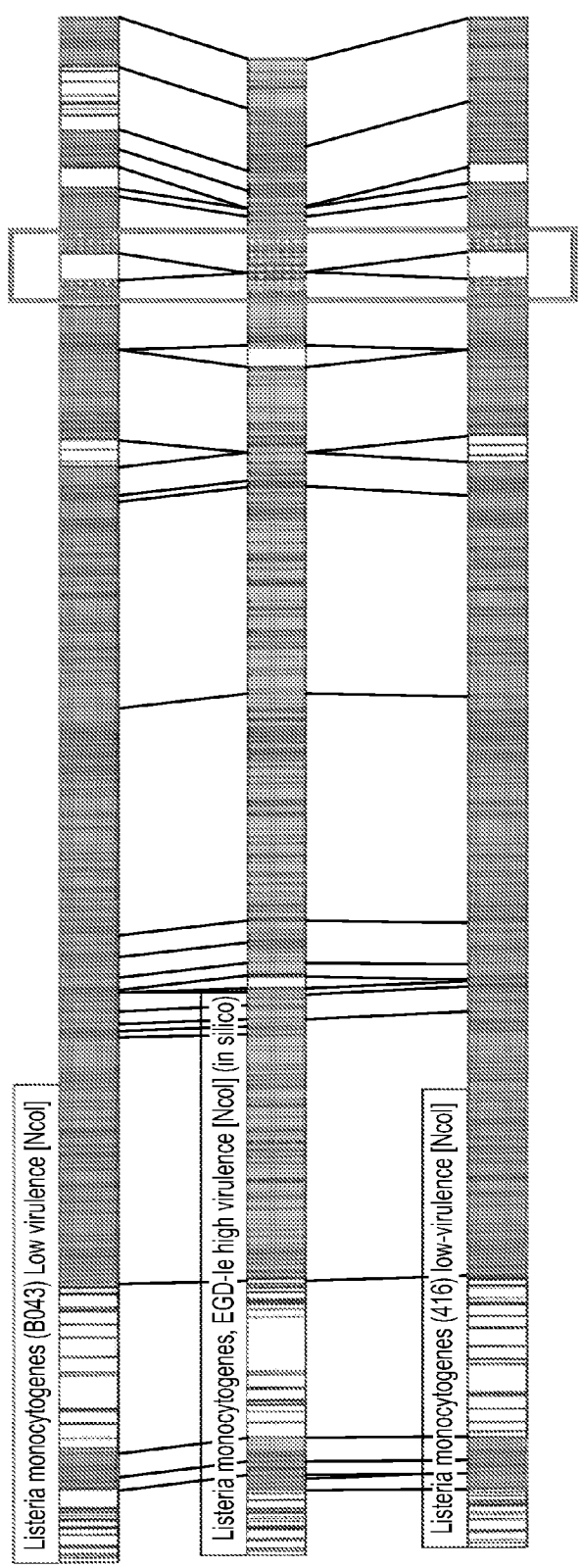
Figure 10:
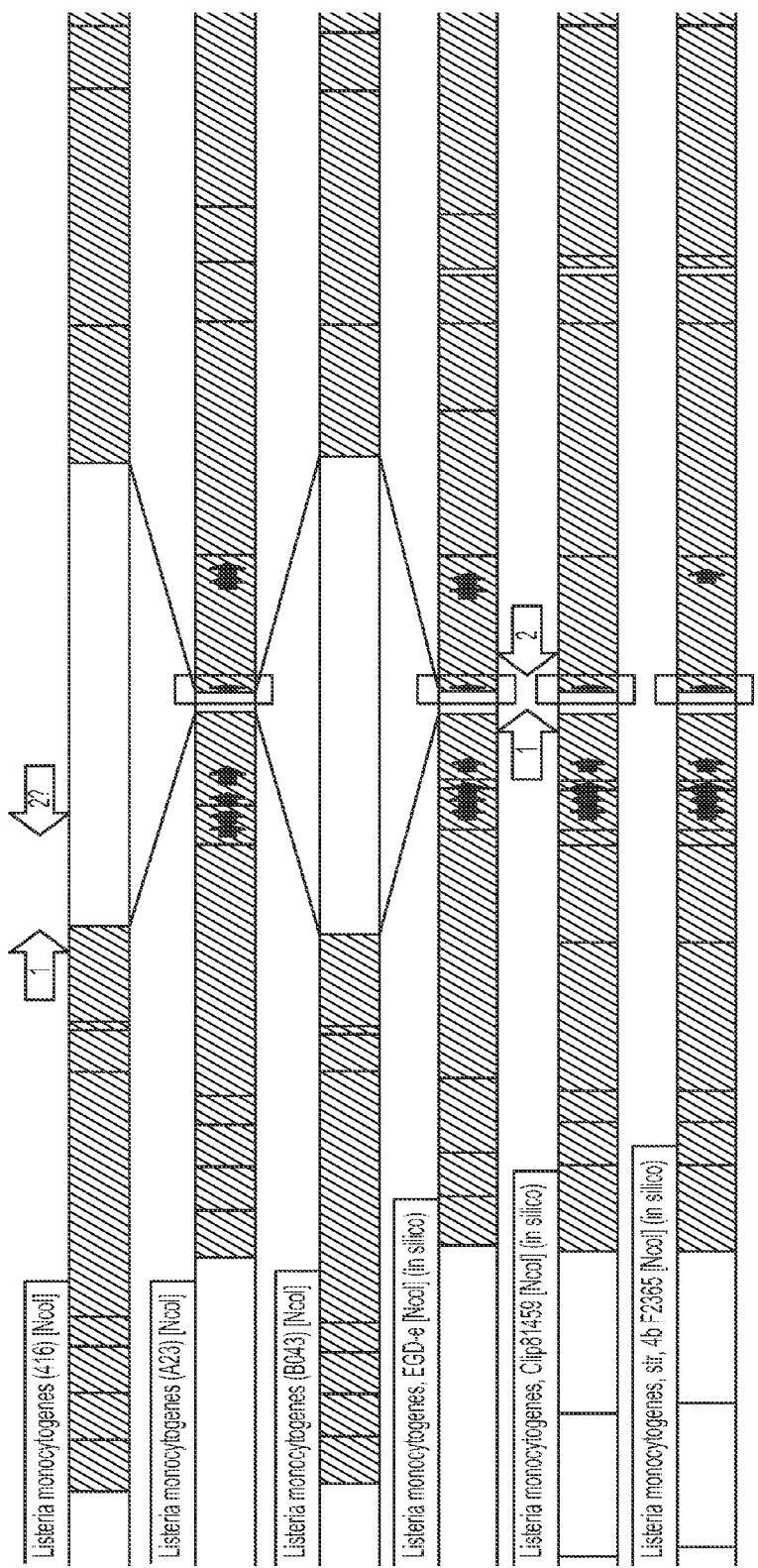
FIG. 10 is a set of optical maps comparing the BO43 and the 416 strains of *L. monocytogenes* to the A23, EDG-e, 4b F2365, and Clip81459 '4b CLIP80459' strains of *L. monocytogenes*. The hatched segments represent regions conserved between the two low virulence strains (BO43 and 416) and the highly virulent strains (A23, EDG-e, 4b F2365, and Clip81459 '4b CLIP80459'). The blank segments represent the insertion in strains 416 and BO43. The boxed region indicates the position of the clpP proteinase gene in the strains.

Upon comparison of the optical maps of these strains of *L. monocytogenes*, it was found that the two low- and/or non-virulent strains of *L. monocytogenes* (BO43 and 416) contain a 48.3 kb insertion in their genomes when compared to the highly virulent strain of *L. monocytogenes* (FIGS. 9-10). It was also determined that this is the sole architectural difference between these two low- and/or non-virulence strains and the highly virulent strains (FIGS. 9-10).

Without being limited by any theory or particular mechanism of action, it is believed that the functional cause of the loss of virulence in these strains is due to insertional inactivation of a virulence gene such as clpP (product ATP-dependent Clp protease proteolytic subunit) which is found in the same approximate location as the insertion site in the sequenced virulent *L. monocytogenes* strain EDG-e. The ATP-dependent caseinolytic proteases (clp) are important in resistance against environmental stresses, antibiotic treatments and host immune defenses for a number of pathogenic bacteria. clpP is the proteolytic subunit, whilst clpA acts both as a chaperone and as an ATPase driving the degradation of damaged or mis-made proteins.

Pathogenic organisms invading a host are exposed to host immune cells and, upon treatment with antibiotics, conditions likely to cause protein damage. Disruption of the clpP gene in strains BO43 and 416 by the inserted DNA may diminish the protein-repair capability of these organisms, resulting in less virulent strains.

These data show that this 48.3 kb region may be used as a marker to distinguish virulent and low- and/or non-virulent strains of *L. monocytogenes*. Methods of the invention use optical mapping as described above to distinguish between virulent and low- or non-virulent strains of *L. monocytogenes*. Methods of the invention involve obtaining a nucleic acid from *L. monocytogenes*; preparing an optical map of one or more restriction digests of the obtained nucleic acid; and detecting an insertion in a clpP gene of a genome of *L. monocytogenes*, wherein presence of the insertion is indicative of a low- or non-virulent strain of *L. monocytogenes*. Therefore, methods of the invention may be used to detect the presence or absence of this insertion in strains of *L. monocytogenes* to predict whether a strain of *L. monocytogenes* is likely to be virulent or low- or non-virulent.

The following examples provide illustrative embodiments of the present methods and should not be treated as restrictive.

Example 1

Microbial Identification Using Optical Mapping

Microbial identification (ID) generally has two phases. In the first, DNA from a number of organisms are mapped and compared against one another. From these comparisons, important phenotypes and taxonomy are linked with map features. In the second phase, single molecule restriction maps are compared against the database to find the best match.

Database Building and Annotation

Maps sufficient to represent a diversity of organisms, on the basis of which it will be possible to discriminate among various organisms, are generated. The greater the diversity in the organisms in the database, the more precise will be the ability to identify an unknown organism. Ideally, a database contains sequence maps of known organisms at the species and sub-species level for a sufficient variety of microorganisms so as to be useful in a medical or industrial context. However, the precise number of organisms that are mapped into any given database is determined at the convenience of the user based upon the desired use to which the database is to be put.

After sufficient number of microorganisms are mapped, a map similarity cluster is generated. First, trees of maps are generated. After the tree construction, various phenotypic and taxonomic data are overlaid, and regions of the maps that uniquely distinguish individual clades from the rest of the populations are identified. The goal is to find particular clades that correlate with phenotypes/taxonomies of interest, which will be driven in part through improvements to the clustering method.

Once the clusters and trees have been annotated, the annotation will be applied back down to the individual maps. Additionally, if needed, the database will be trimmed to include only key regions of discrimination, which may increase time performance.

Calling (Identifying) an Unknown

One embodiment of testing the unknowns involves comparing each of the raw single molecule maps from the unknown sample against each of the entries in the database, and then combining match probabilities across different molecules to create an overall match probability.

The discrimination among closely related organisms can be done by simply picking the most hits or the best match probability by comparing data obtained from the organism to data in the database. More precise comparisons can be done by having detailed annotations on each genome for what is a discriminating characteristic of that particular genome versus what is a common motif shared among several isolates of the same species. Thus, when match scores are aggregated, the level of categorization (rather than a single genome) will receive a probability. Therefore, extensive annotation of the genomes in terms of what is a defining characteristic and what is shared will be required.

In one embodiment of the method, entire genomes will be compared to all molecules. Because there will generally be much overlap of maps within a species, another embodiment can be used. In the second embodiment, several methods of extracting shared elements from the genome will be created to generate a reduced set of regions that can still serve as a reference point for the matching algorithms. The second embodiment will allow for streamlining the reference database to increase system performance.

Example 2

Using Multiple Enzymes for Microbial Identification

In one embodiment, the single molecule restriction maps from each of the enzymes will be compared against the database described in Example 1 independently, and a probable identification will be called from each enzyme independently. Then, the final match probabilities will be combined as independent experiments. This embodiment will provide some built-in redundancy and therefore accuracy for the process.

Introduction

In general, optical mapping can be used within a specific range of average fragment sizes, and for any given enzyme there is considerable variation in the average fragment size across different genomes. For these reasons, it typically will not be optimal to select a single enzyme for identification of clinically-relevant microbes. Instead, a small set of enzymes will be chosen to optimize the probability that for every organism of interest, there will be at least one enzyme in the database suitable for mapping.

Selection Criteria

A first step in the selection of enzymes was the identification of the bacteria of interest. These bacteria were classified into two groups: (a) the most common clinically interesting organisms and (b) other bacteria involved in human health. The chosen set of enzymes must have at least one enzyme that cuts each of the common clinically interesting bacteria within the range of average fragment sizes suitable for detailed comparisons of closely related genomes (about 6-13 kb). Additionally, for the remaining organisms, each fragment must be within the functional range for optical mapping (about 4-20 kb). These limits were determined through mathematical modeling, directed experiments, and experience with customer orders. Finally, enzymes that have already been used for Optical Mapping were selected.

Suggested Set

Based upon the above criteria, the preliminary set consisted of the enzymes BglII, NcoI, and XbaI, which have been used for optical mapping. There are 28 additional sets that cover the key organisms with known enzymes, so in the event that this set is not adequate, these alternatives will be utilized (data not shown).

Final Steps

Because the analysis in Experiment 2 is focused on the sequenced genomes, prior to full database production, this set of enzymes will be tested against other clinically important genomes, which will be part of the first phase of the proof of principle study.

Example 3

Identification of *E. coli*

A. In one embodiment of a microbial identification method, nucleic acids of between about 500 and about 1,000 isolates will be optically mapped. Then, unique motifs will be identified across genus, species, strains, substrains, and isolates. To identify a sample, single nucleic acid molecules of the sample will be aligned against the motifs, and p-values assigned for each motif match. The p-values will be combined to find likelihood of motifs. The most specific motif will give the identification.

Figure 2:
FIG. 2 is a diagram showing restriction maps of six isolates of *E. coli* clustered into three groups: O157 (that includes O157:H7 and 536), CFT (that includes CFT073 and 1381), and K12 (that includes K12 and 718).

B. The following embodiment illustrates a method of identifying *E. coli* down to an isolate level. Restriction maps of six *E. coli* isolates were obtained by digesting nucleic acids of these isolates with BamHI restriction enzyme. FIG. 1 shows restriction maps of these six *E. coli* isolates: 536, O157:H7 (complete genome), CFT073 (complete genome), 1381, K12 (complete genome), and 718. As shown in FIG. 2, the isolates clustered into three sub-groups (strains): O157 (that includes O157:H7 and 536), CFT (that includes CFT073 and 1381), and K12 (that includes K12 and 718).

Figure 3:
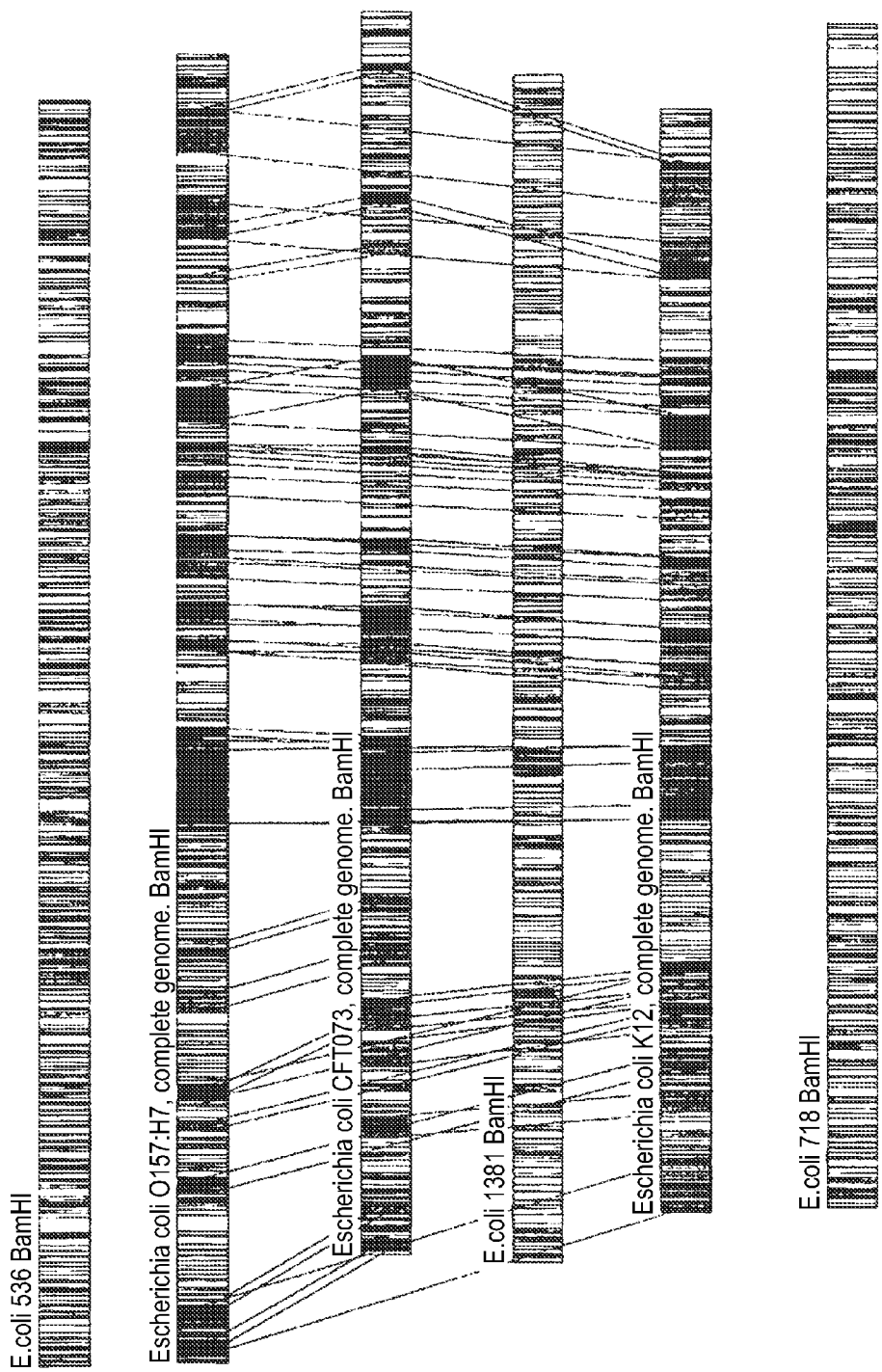
FIG. 3 is a diagram showing common motifs among restriction maps of six isolates of *E. coli*.
Figure 4:
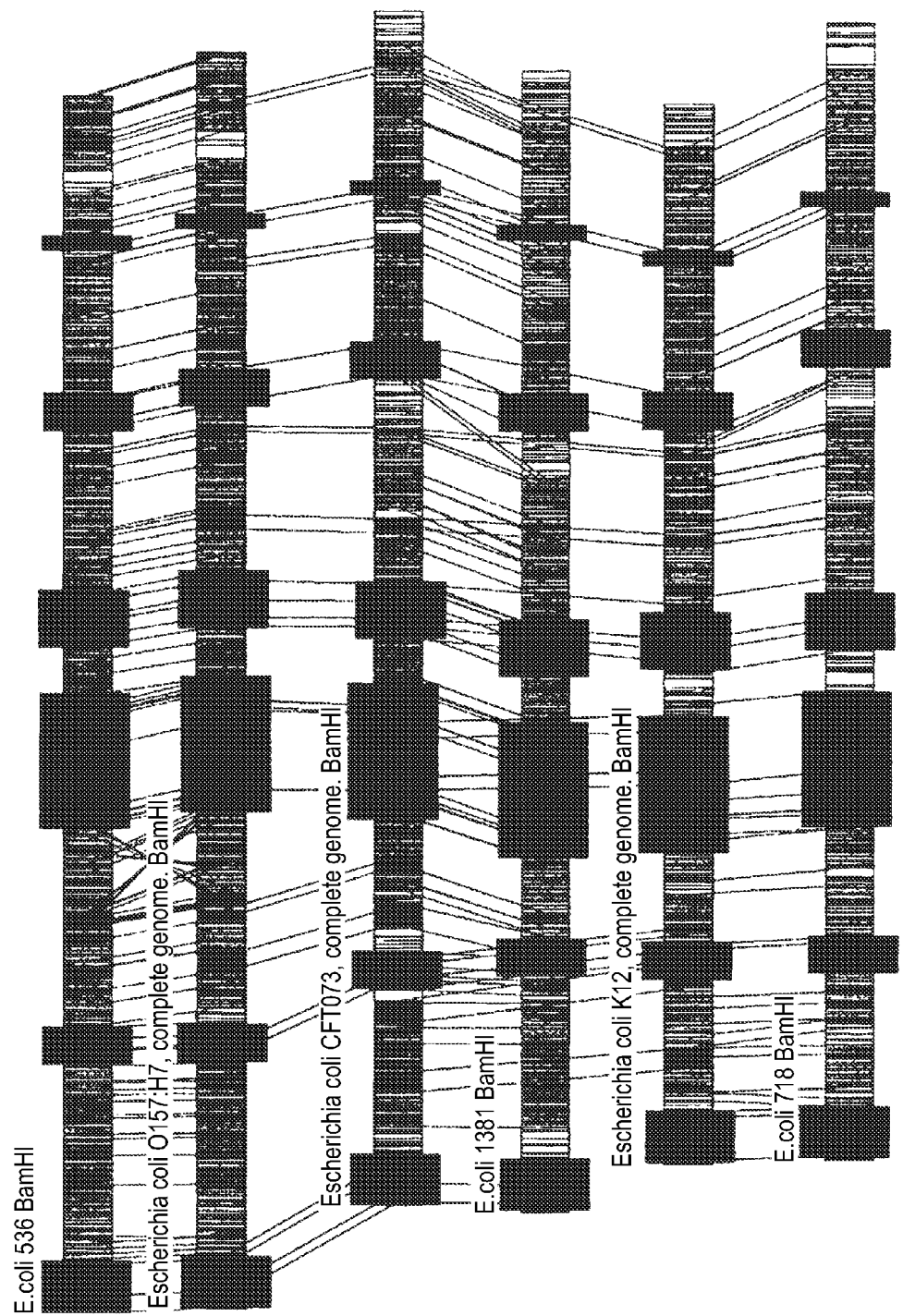
FIG. 4 is a diagram showing restriction maps of six isolates of *E. coli*, with the boxes indicating regions common to *E. coli*.
Figure 5:
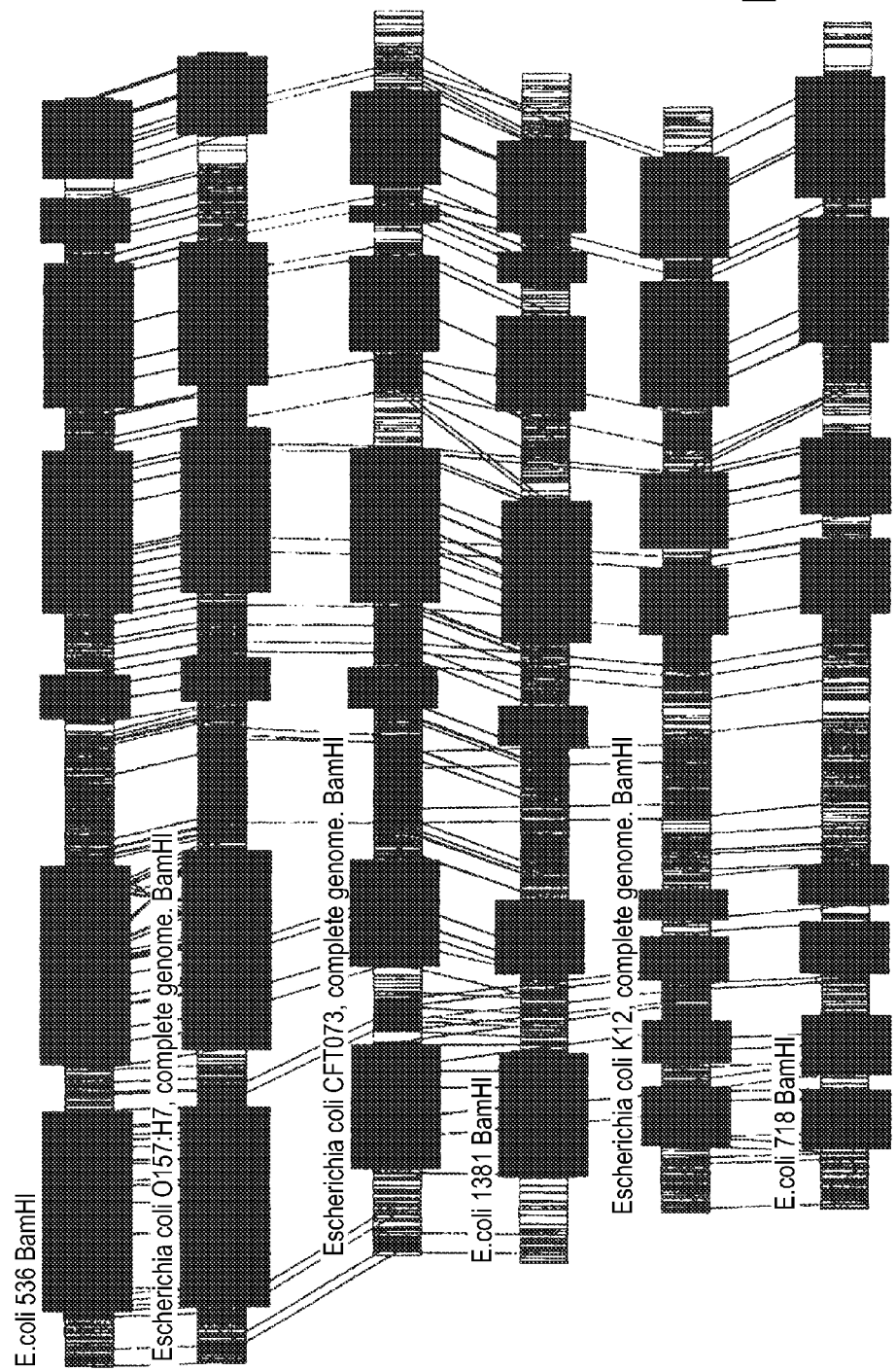
FIG. 5 is a diagram showing restriction maps of six isolates of *E. coli*, with the boxes indicating regions that are unique to a particular strain, namely O157, CFT, or K12.

These restriction maps provided multi-level information regarding relation of these six isolates, e.g., showed motifs that are common to all of the three sub-groups (see, FIG. 3) and regions specific to *E. coli* (see, boxed areas in FIG. 4). The maps were also able to show regions unique to each strain (see, boxed areas in FIG. 5) and regions specific to each isolate (see boxed regions in FIG. 6).

Figure 6:
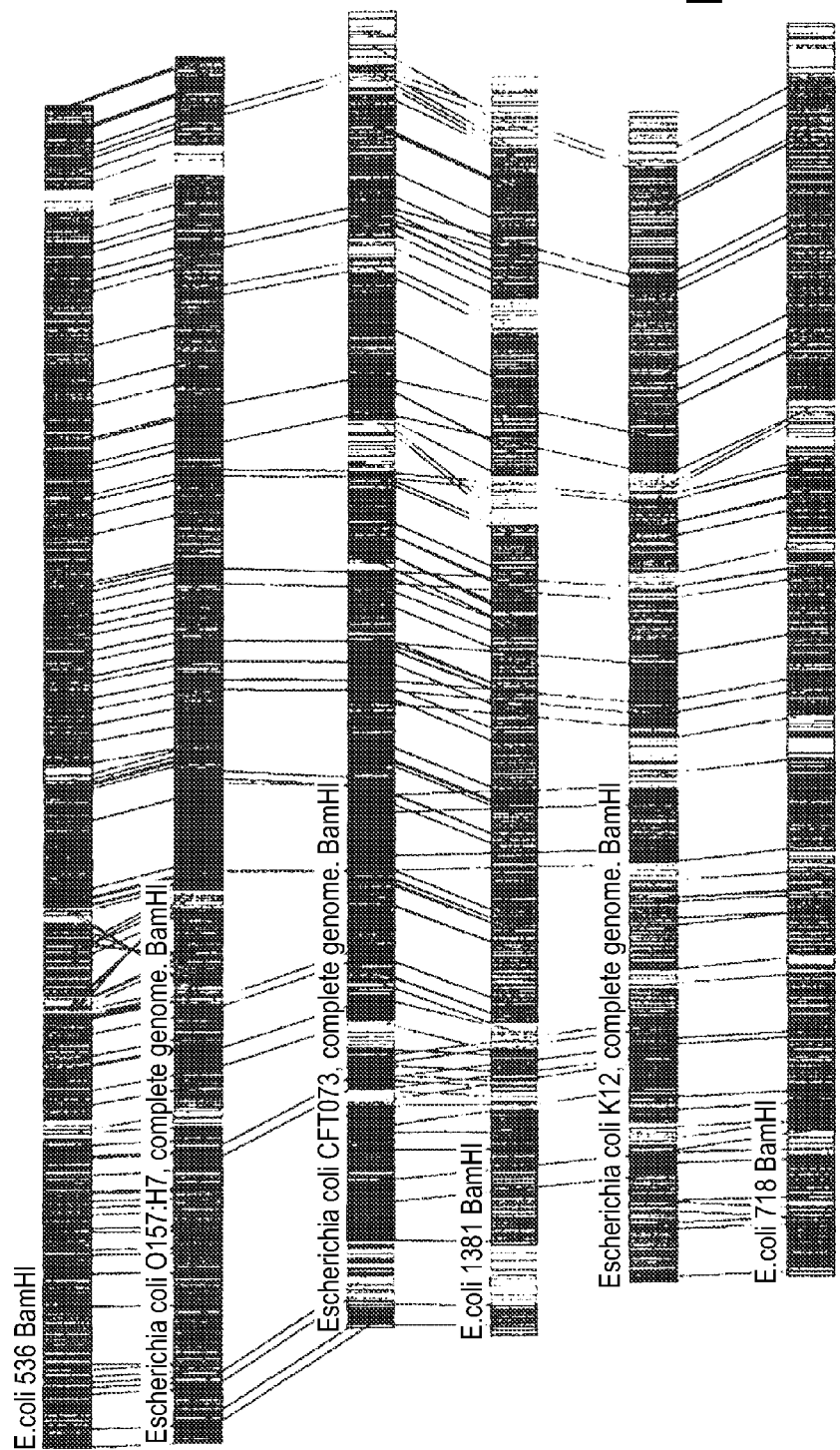
FIG. 6 is a diagram showing restriction maps of six isolates of *E. coli*, with the boxes indicating regions unique to each isolate.
Figure 7:
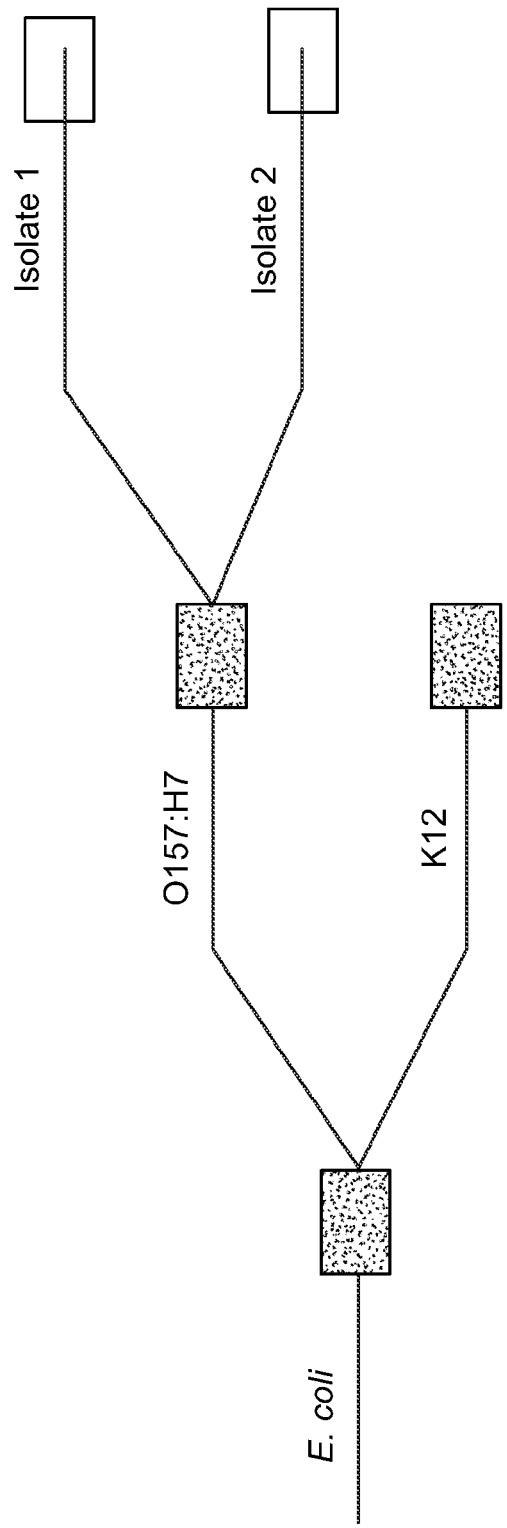
FIG. 7 is a tree diagram, showing possible levels of identifying *E. coli*.

This and similar information can be stored in a database and used to identify bacteria of interest. For example, a restriction map of an organism to be identified can be obtained by digesting the nucleic acid of the organism with BamHI. This restriction map can be compared with the maps in the database. If the map of the organism to be identified contains motifs specific to *E. coli*, to one of the sub-groups, to one of the strains, and/or to a specific isolate, the identity of the organism can be obtained by correlating the specific motifs. FIG. 6 shows a diagram to illustrate the possibilities of traversing variable lengths of a similarity tree.

Figure 8:
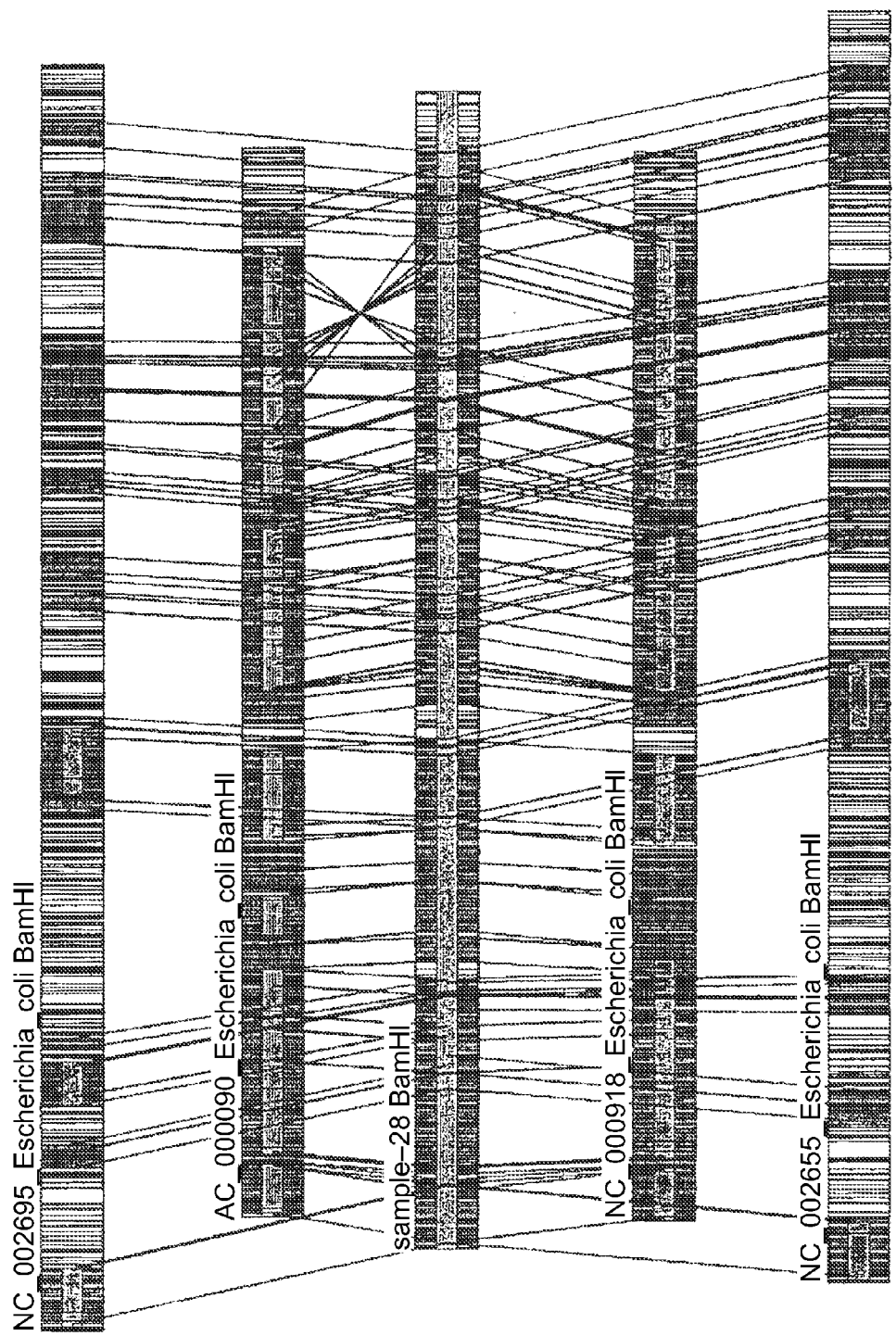
FIG. 8 is a diagram showing restriction maps of a sample (middle map) and related restriction maps from a database.

C. The following example illustrates identifying a sample as an *E. coli* bacterium. A sample (sample 28) was digested with BamHI and its restriction map obtained (see FIG. 8, middle restriction map). This sample was aligned against a database that contained various *E. coli* isolates. The sample was found to be similar to four *E. coli* isolates: NC 002695, AC 000091, NC 000913, and NC 002655. The sample was therefore identified as *E. coli* bacterium that is most closely related to the AC 000091 isolate.

The embodiments of the disclosure may be carried out in other ways than those set forth herein without departing from the spirit and scope of the disclosure. The embodiments are, therefore, to be considered to be illustrative and not restrictive. References and citations to other documents, such as patents, patent applications, patent publications, journals, books, papers, web contents, have been made throughout this disclosure. All such documents are hereby incorporated herein by reference in their entirety for all purposes.

What is claimed is:

1. A method of distinguishing virulent and low- or non-violent strains of *Listeria monocytogenes*, the method comprising:
    obtaining a nucleic acid from *L. monocytogenes*;
    preparing an optical map of one or more restriction digests of the obtained nucleic acid; and
    detecting an insertion that is at least 48.3 kb in size in a clpP gene of a genome of *L. monocytogenes*, wherein presence of the insertion is indicative of a low- or non-virulent strain of *L. monocytogenes*.

2. The method according to claim 1, wherein the nucleic acid is obtained from at least one sample type selected from the group consisting of: a food sample, an environmental sample, and a human tissue or body fluid sample.

3. The method according to claim 2, wherein the environmental sample is selected from the group consisting of water, soil, sewage, and decaying vegetable matter.

4. The method according to claim 2, wherein the tissue or body fluid is from a human having a disease selected from the group consisting of meningitis, gastroenteritis, and septicemia.

5. The method according to claim 1, wherein the *L. monocytogenes* is classified as a serotype 4b strain.

6. The method according to claim 1, wherein the *L. monocytogenes* is classified as a serotype 1/2a strain.

7. The method according to claim 1, wherein the *L. monocytogenes* low- or non-virulent strain is selected from the group consisting of *L. monocytogenes* BO43 or *L. monocytogenes* 416.

8. The method according to claim 1, wherein the *L. monocytogenes* virulent strain is selected from the group consisting of *L. monocytogenes* strain 4b F2365, *L. monocytogenes* strain EGD-e, *L. monocytogenes* strain A23, *L. monocytogenes* Clip81459 '4b CLIP80459'.

* * * * *